United States Patent
Pekarske et al.

(10) Patent No.: US 10,362,372 B2
(45) Date of Patent: Jul. 23, 2019

(54) SYSTEM AND METHOD OF SELECTING WIRELESS SPECTRUM AND PROTOCOL BASED ON PATIENT ACUITY

(71) Applicant: General Electric Company, Schenectady, NY (US)

(72) Inventors: Matthew Richard Pekarske, Milwaukee, WI (US); SM S. Hasan, Niskayuna, NY (US); Bruce Arnold Friedman, Jasper, GA (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 420 days.

(21) Appl. No.: 14/143,555

(22) Filed: Dec. 30, 2013

(65) Prior Publication Data

US 2015/0189404 A1 Jul. 2, 2015

(51) Int. Cl.
*H04Q 9/00* (2006.01)
*G08C 25/00* (2006.01)
*A61B 5/00* (2006.01)

(52) U.S. Cl.
CPC ............... *H04Q 9/00* (2013.01); *G08C 25/00* (2013.01); *A61B 5/0022* (2013.01)

(58) Field of Classification Search
CPC .......................................................... H04Q 9/00
USPC .................................................... 340/870.07
See application file for complete search history.

(56) References Cited

U.S. PATENT DOCUMENTS

| | | | |
|---|---|---|---|
| 8,358,590 B2* | 1/2013 | Pekarske | A61B 5/002 370/252 |
| 8,422,463 B2* | 4/2013 | Pekarske | H04L 1/0002 370/333 |
| 8,422,464 B2* | 4/2013 | Friedman | H04L 1/0007 370/252 |
| 2008/0208623 A1* | 8/2008 | Fahey | G06Q 50/22 705/2 |
| 2008/0228045 A1* | 9/2008 | Gao | A61B 5/0024 600/301 |
| 2009/0268703 A1* | 10/2009 | Furumi | H04W 76/18 370/342 |
| 2011/0032822 A1* | 2/2011 | Soomro | H04W 72/10 370/230 |
| 2011/0169644 A1* | 7/2011 | Muhsin | G08B 25/008 340/573.1 |
| 2013/0007853 A1* | 1/2013 | Gupta | H04W 76/10 726/5 |
| 2013/0018239 A1* | 1/2013 | Lisogurski | A61B 5/0004 600/322 |
| 2013/0035871 A1* | 2/2013 | Mayou | A61B 5/14532 702/26 |

(Continued)

*Primary Examiner* — Amine Benlagsir
(74) *Attorney, Agent, or Firm* — Andrus Intellectual Property Law, LLP (57) ABSTRACT

As the acuity level of a patient being monitored on a wireless system changes, the criticality of that patient's data arriving at its intended destination changes. For example, if a patient being monitored for potentially life threatening arrhythmias begins to decline in health while being monitored on a less reliable wireless system, the wireless monitor switches to a more reliable wireless system to ensure delivery of critical patient data. Allowing a patient monitor to switch between wireless infrastructures based on patient acuity limits the number of users operating on the higher cost wireless infrastructure.

16 Claims, 5 Drawing Sheets

(56) References Cited

U.S. PATENT DOCUMENTS

2013/0111002 A1* 5/2013 Leber ............... H04L 69/08
                                                                              709/223
2013/0337749 A1* 12/2013 Wang ............... H04W 4/80
                                                                              455/41.2

* cited by examiner

SYSTEM AND METHOD OF SELECTING WIRELESS SPECTRUM AND PROTOCOL BASED ON PATIENT ACUITY

FIELD

The present application is directed to the field of patient monitoring systems. More specifically, the present application, is directed to wireless patient monitoring systems having multiple wireless infrastructures.

BACKGROUND

In certain networked environments, such as medical facility networks involving patient monitoring over Wireless Local Area Network (WLANs), it is desirable to leverage an existing investment of a common network to deploy wireless bedside and telemetry applications. However, as more and more wireless clients access the WLAN, the network may become congested, with different types of devices competing for priority on the WLAN. Such interference and increased usage from multiple devices in wireless bands degrades overall network performance and can lead to gaps in critical patient data and dropouts or delays in delivering alarms that can impact patient safety. For example, a patient-worn telemetry device set up to monitor a high-acuity patient for potentially life-threatening arrhythmia may be transmitting data on the WLAN, but may not be equipped with a local alarm to alert caregivers to a change in the patient's condition. It is critical that the patient data and alarm messages from such a device be routed to, for example, a remote central monitoring station or portable electronic device carried by a caregiver in real-time over the WLAN. There may also be multiple bedside monitors competing for access to the WLAN that, by contrast, may be equipped with local alarms to alert caregivers to a change in conditions, such that any delay in transmission of an alarm on the network may not be as critical to patient safety. Furthermore, the respective acuity levels of the various patients being monitored by the various wireless monitoring devices on the WLAN may be constantly changing, and the delay of data from a lower acuity patient being monitored by it patient-worn telemetry device may not be as critical to patient safety as a delay of data from a higher-acuity patient. In the absence of effective means for prioritizing transmission of the patient data and alarm messages among these various devices, the more critical data may be delayed or lost.

The Institute of Electronic and Electrical Engineers (IEEE) 802.11 standard for wireless LANs is a popular mechanism for setting up networks in many industrial, office, home and medical environments. The main limitation of the legacy 802.11 is that it cannot support priority classifications to differentiate among different types of traffic. That is, every type of traffic is treated with equal fairness in the network. A newer standard called 802.11e has emerged which has prioritized traffic delivery for differentiating among traffic at different levels of criticality. The 802.11e standard achieves this by having a differentiated services control parameter in the IP layer for controlling wireless communication. For example, a six-bit Differentiated Services Code Point (DCSP) may be assigned at the IP layer and used in the MAC layer to classify and prioritize types of traffic. Using the DSCP parameter for lower and higher priority traffic classes, the higher priority traffic class is assigned shorter wait times for transmission across the WLAN. However, even though 802.11e can differentiate among traffic classes, under standard operating, conditions, the 802.11e DSCP parameter is static in nature, meaning that it is not optimal under all monitoring scenarios. For example, when a change in the status or condition of a patient being monitored over a medical facility WLAN occurs, the 802.11e DSCP parameter does not adapt to those changing conditions. This makes the 802.11e DSCP default parameters unsuitable for some applications, such devices used for patient monitoring in a medical facility, where dropouts and delays in delivering alarms can impact patient safety.

Different wireless infrastructures have different levels of cost (install, maintenance) and reliability (acceptable packet loss, delay, jitter, and throughput). WLAN such as the IEEE 802.11e standard described above are more commonly available and thus used by many commercially available devices. However, these WLANs may not have the reliability required to send critical data from a patient with a high acuity level. Wireless Medical Telemetry Services (WMTS) and Medical Body Area Network (MBAN) wireless infrastructures come with a higher cost, but allow for a higher level of reliability.

Furthermore, in certain networked environments, such as medical facility networks involving patient monitoring over WLANs, it is desirable to leverage an existing investment in a common network to deploy wireless bedside and telemetry applications. However, as more and more wireless clients access the WLAN, the network may become congested, with different types of devices competing for priority on the WLAN. Such interference increased usage from multiple devices in wireless bands degrades overall network performance and can lead to gaps in critical patient data and dropouts or delays in delivering alarms that can impact patient safety.

Accordingly, there is need for improved systems, devices and methods of data prioritization to increase the reliability of data transmission over WLANs and to ensure robust transmission of critical data, such as patient data in medical monitoring applications for varying acuity levels of patients.

SUMMARY

The above-mentioned shortcomings, disadvantages and problems are addressed herein which will be understood by reading and understanding the fallowing specification.

As the acuity level of a patient being monitored on a wireless system changes, the criticality of that patient's data arriving at its intended destination changes. For example, if a patient being monitored for potentially life threatening arrhythmias begins to decline in health while being monitored on a less reliable wireless system, the wireless monitor switches to a more reliable wireless system to ensure delivery of critical patient data. Allowing a patient monitor to switch between wireless infrastructures based on patient acuity limits the number of users operating on the higher cost wireless infrastructure.

In one aspect of the present application, a method of controlling transmission of patient data over a wireless network comprises assessing an acuity level of the patient data, and transmitting the patient data over the network based on the assessed acuity level for such patient.

In another aspect of the present application, a node configured for wireless communication of patient data with an access point, the node comprises a controller configured to receive the patient data, assess an acuity level of the patient data, and transmit the patient data based on the assessed acuity level of the patient data.

In another aspect of the present application, a network comprises an access point, and nodes configured for wireless communication of patient data with the access point, wherein each of the nodes include a controller configured to receive the patient data, assess an acuity level of the patient data, and transmit the patient data over the network based on the acuity level of the patient data, further wherein the controller is configured to assess the acuity level by comparing the patient data to a set of acuity limits, assigning a classification to the patient data based on the comparison, applying a set of statistical values to the patient data based on the classification, and conducting a weighted sum calculation on the weighted patient data, wherein the weighted sum calculation outputs the acuity level.

Various other features, objects, and advantages of the invention will be made apparent to those skilled in the art from the accompanying drawings and detailed description thereof.

DETAILED DESCRIPTION

In the present description, certain terms have been used for brevity, clearness and understanding. No unnecessary limitations are to be applied therefrom beyond the requirement of the prior art because such terms are used for descriptive purposes only and are intended to be broadly construed. The different systems and methods described herein may be used alone or in combination with other systems and methods. Various equivalents, alternatives and modifications are possible within the scope of the appended claims. Each limitation in the appended claims is intended to invoke interpretation under 35 U.S.C. § 112, sixth paragraph, only if the terms "means for" or "step for" are explicitly recited in the respective limitation.

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

As the acuity of the patient being monitored on a wireless system changes, the criticality of that patient's data arriving at its intended destination changes. For example, if a patient being monitored for potentially life threatening arrhythmias begins to decline in health while being monitored on a less reliable wireless system, the wireless monitor should switch to a more reliable wireless system to ensure delivery of critical patient data.

In an environment where multiple wireless infrastructures are present, for example Wireless Local Area Network (WLAN), Wireless Medical Telemetry Service (WMTS), and Medical Body Area Network (MBAN), the patient monitoring device must be able to connect to all or some of these technologies. Furthermore, the patient monitoring device needs a method to determine patient acuity and utilize the patient acuity level to select the appropriate wireless infrastructure to use. For example, a patient with a high acuity level would use highly reliable wireless infrastructure.

Figure 1:
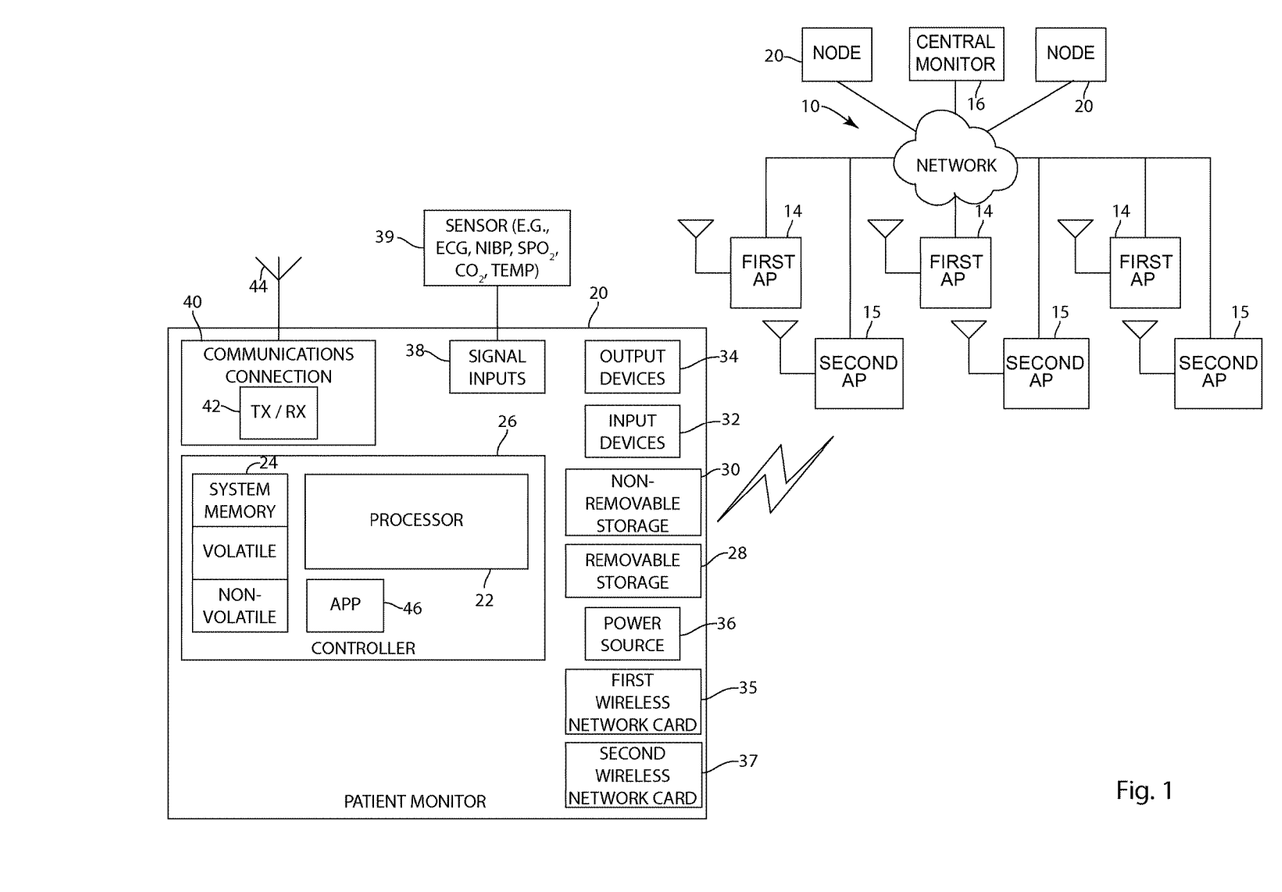
FIG. 1 is a schematic illustration of a network in accordance with an exemplary embodiment.

Referring to FIG. 1, a schematically represented network 10 is shown. Wireless network 10 is generally configured to facilitate wireless communication among two or more nodes 20, as well as other types of devices set up to access network 10. By way of example, network 10 may be a WLAN, wherein various nodes 20 are configured to communicate wirelessly over network 10 according to IEEE 802.11e protocol via one or more access points (APs) 14, 15. Node 20 may be in a state of searching for devices that belong to network 10 by periodically scanning actively and by sending probe requests and scanning for probe response signals transmitted by access point 14, 15. Alternatively, node 20 may search passively by scanning for beacons transmitted by access point 14, 15. According to an embodiment involving patient monitoring over a WLAN in a medical facility, network 10 may include one or more types of nodes 20 (e.g., DASH or APEX PRO monitoring devices manufactured by General Electric Company) monitoring patients of varying acuity levels. The nodes 20 may be communicating patient data to a central monitoring station 16 (e.g., a CIC PRO central monitoring station manufactured by General Electric Company) over network 10 via one or more access points 14, 15 according to various protocols. The access points 14, 15 include a set of first access points 14 having a first wireless protocol to communicate with a first wireless network card 35, and a set of second access points 15 having a second wireless protocol for communication with a second wireless network card 15. Of course, it is contemplated that a network 10 may include more than two wireless protocols for communicating data from a node 20. Such networks 10 would include more than two sets of access points 14, 15 and corresponding network cards 35, 37.

Node 20 is configured fir access to a network 10. In its most basic configuration, node 20 includes at least a processing unit 22 and a memory 24. Depending on the exact configuration and type of computing device, memory 24 may be volatile (such as RAM), nonvolatile (such as ROM, flash memory, etc.) or some combination of the two. Processing unit 22 and memory 24 are included in, and form part of, a controller 26.

Node 20 may also have additional features/functionality. For example, node 20 may also include additional storage (removable and/or non-removable) including, but not limited to, magnetic or optical disks or tapes. Such additional storage is illustrated in FIG. 1 by a removable storage 28 and a non-removable storage 30. Computer storage media includes volatile and nonvolatile, removable and non-removable media implemented in any method or technology for storage of information such as computer readable instructions, data structures, program modules or other data. Node 20 may also have one or more input devices 32 such as keyboard, mouse, pen, voice input device, touch-input device, etc. One or more output devices 34 such as a display, speakers, printer, etc. may also be included. Node 20 may also be provided with a power source 36, such as a battery pack or the like. Power source 36 provides power for computations and wireless data transmissions by node 20.

Node 20 may also include analog or digital signal inputs 38. According to an embodiment wherein node 20 is a patient monitoring device, signal inputs 38 may be a data acquisition component including, for example, signal acquisition hardware (e.g., signal amplifiers, galvanic isolation components, analog-to-digital converters, etc.) and a software application executed by processing unit 22 to receive data from the signal acquisition hardware and perform further processing. In this embodiment, signal inputs 38 may be coupled to a patient by an array of sensors or transducers 39, such as, for example, electrocardiogram (ECG) leads, invasive or noninvasive blood pressure devices, temperature probes, blood gas measurement probes, airway gas sensors, and patient location and position sensors in order to receive patient data.

Node 20 may also contain one or more communications connections 40 that allow node 20 to communicate with other devices. Communications connection 40 provides for communication with a WLAN via, for example, acoustic, RF, infrared and other wireless media. As discussed above, the term computer readable media as used herein includes both storage media and communication media By way of example, communications connection 40 may include a network interface card (NIC), such as a USB or SD wireless card for wirelessly communicating, with different types of wireless networks. The NIC includes a transceiver 42 that is coupled to an antenna 44 for transmitting and receiving data wirelessly over a suitable frequency channel. According to an embodiment, communications connection 40 employs wireless configuration service over IEEE 802.11e wireless connections to ease network configuration, including infrastructure networks and ad hoc networks. Further in this embodiment, there are two additional communication connections 40, namely a first and second wireless network card 35, 37. As stated previously, these wireless network cards 35, 37 may be configured to connect with corresponding wireless access points 14, 15. For this embodiment, the first wireless network card 35 and first wireless access point 14 allow the node 20 to utilize a wireless network with a higher reliability, relative to the network utilized by the second wireless network card 35 and the second wireless access point 15.

Communications connection 35, 37, 40 may also include hardware and/or software configured to evaluate the signal quality of network 10 between node 20 and, for example, access point 14, 15. By way of example, communications connection 35, 37, 40 may be configured to measure a signal-to-noise ratio (SNR) for transmissions in the format of a power ratio between a signal transmitted over network 10 and background noise. Similarly, communications connection 40 may be configured to measure a received signal strength indicator (RSSI) indicative of the power present in signals transmitted over network 10. Communications connection 40 may also be configured to measure a noise floor value indicative of the lowest input signal power that can be recognized as a recoverable information signal by node 20. Communications connection 35, 37, 40 may also be configured to determine a retransmission rate indicative of a number of transmission retries by node 20. Communications connection 35, 37, 40 may also be configured to determine a number of missed beacon signals from, for example, AP 14, 15. Other types of signal quality measurements are anticipated as well.

Referring still to FIG. 1, controller 26 includes an application 46 for processing patient data received by, acquired by or stored on node 20 in order to assign a priority level to the data packets containing the patient data. The term "patient data" as used herein generally refers to the actual information to be communicated to an end user via a data packet, such as, for example, patient parameter, alarm or waveform. The term "data" as used herein generally refers to different types of payload data unless otherwise specified. The term "payload" as used herein generally refers to the portion of a data packet containing payload data. According to an embodiment, application 46 compares this data to defined acuity limits to determine an acuity classification for the data and then performs a weighted sum calculation in order to determine the priority level.

Figure 2:
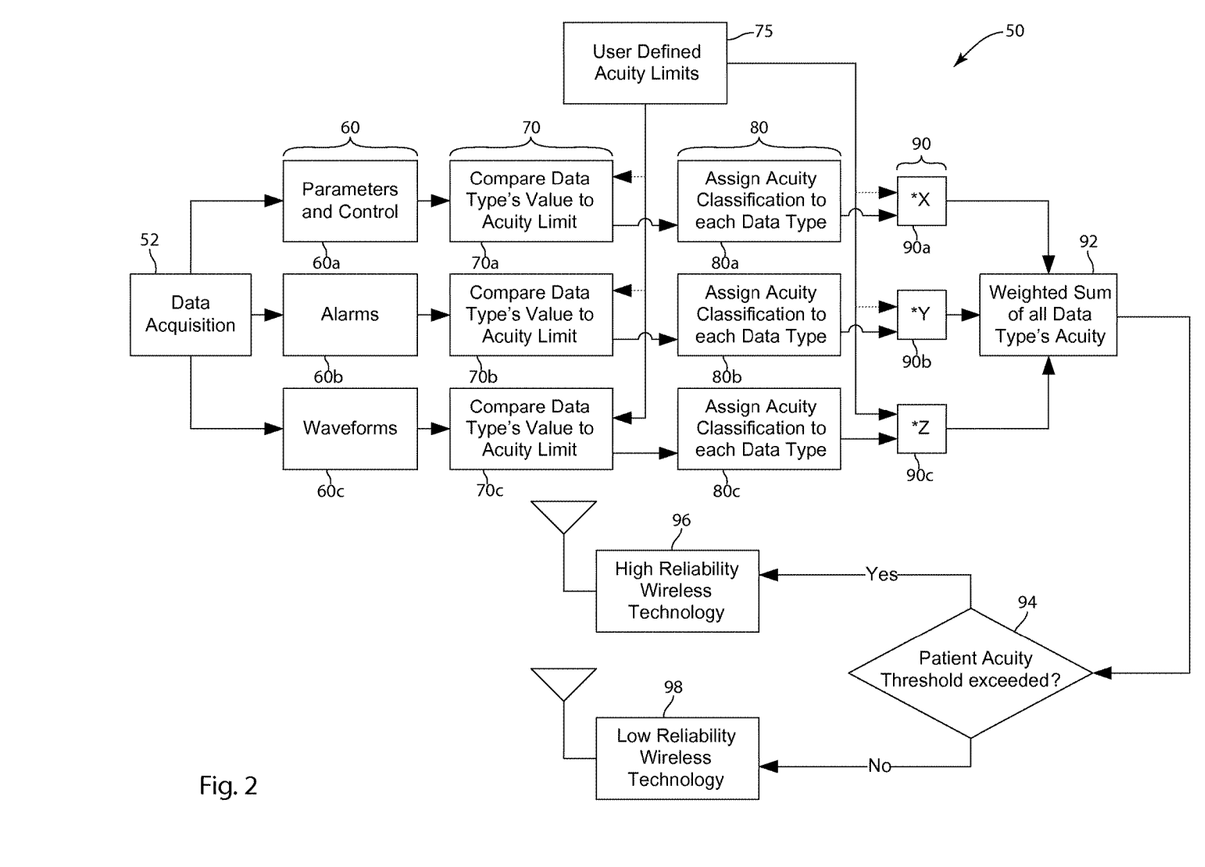
FIG. 2 is a block diagram illustrating an exemplary computer implemented process of selecting wireless spectrum and protocol based on patient acuity in the network.

Referring now to FIG. 2, a block diagram illustrating, a computer-implemented process 50 for providing wireless protocol prioritization of data in network 10 is shown. In an embodiment, process 50 is directed to determining whether collected data 52 from a patient should be transmitted over a higher reliability protocol network 96 or a relatively lower reliability protocol network 98. The process 50 of FIG. 2 determines this by assigning an acuity sum of all the data 52 acquired from the patient and determining, whether the patient's acuity level 92 exceeds a user-determined acuity threshold 94. This threshold may be set by a user, may be set to a default threshold or industry standard, or any method known in the art.

While FIG. 2 is described and shown with respect to the acuity level and threshold of a patient and connecting to a higher reliability network when the threshold is exceeded by taking into account parameters and control, alarms and waveforms, it is also envisioned that other or additional parameters could be considered. Additionally, it is further envisioned that process 50 could be applied to other wireless communication protocols beyond 802.11e, such as updated 802.11 protocols (e.g., 802.11n), and to more than two levels of reliability, i.e., three, four or more wireless network reliability levels. Furthermore, while FIG. 2 is described in the context of node 20 as a patient monitoring, device transmitting patient data over a network 10 in a medical facility, it is envisioned that process 50 is applicable other types of nodes and networked applications.

Referring to FIG. 2, in process 50 at an individual node 20, controller 26 receives data 52 to be transmitted over network 10. The data 52 may be, for example, data 52 acquired by node 20 or data previously stored on node 20. According to an embodiment wherein node 20 is a patient monitoring device transmitting patient data 52 over network 10 in a medical facility, it is envisioned that the acquired data 52 may include a number of data types 60, for example, parameter and control data 60*a*, alarm data 60*b* and waveform data 60*c*. Parameter and control data 60*a* may include, for example, discrete (e.g., digital) values of physiologic vital sign data such as heart rate or electrocardiogram (ECG) data, blood pressure data (invasive or noninvasive), temperature data, blood gas measurement data (e.g., Sp02 data), and airway gas measurement data (e.g., CO2 data). Parameter and control data 60 may also include data that reflects patient movement. For example, if a patient is convulsing or walking around, or lying completely still, this parameter and control data 60*a* may be utilized in determining an acuity level of a patient. Alarm data 60*b* may include, for example, data indicating that certain parameter and control data 60*a* for a patient has exceeded a predetermined limit and that assistance may be required (e.g., the patient has an excessive heart rate or temperature higher than normal body temperature). Alarm data 60*b* may also include data indicating a change in the state of the node 20 (e.g., sensor 39 has become disconnected or power source 36 is nearly discharged). Waveform data 60*c* may include, for example, analog or continuous patient physiological data, such as an ECG waveform, sent at an appropriate data resolution for review by a caregiver. Other types of data 52 may include, for example, electronic medical record (EMR) data that may be important to monitoring the patient's condition and the locations of the node 20, for example on ICU, maternity or stepdown care.

In the illustrated implementation of process 50 in FIG. 2, application 46 processes the data 52 received by controller 26 for transmission over network 10 and determines a priority level for the data 52. In particular, application 46 compares values 70 of data 60 with a user pre-defined acuity limit 75 in order to determine an acuity classification 80 for the data 52. These user-defined acuity limits may also be set by a user, may be set to default threshold or industry standard, or any method known in the art. Data values 70 for each type of data type 60 may be established based on, for example, critical levels or ranges into which values of data type 60 may fall. There may be a single data value 70 for each type of data type 60, or multiple data values 70 establishing a range of data values 70 for each data type 60.

Application 46 dotes dines an acuity classification 80 for data type 60 based on the comparison of the data value 70 to the acuity limits 75. For example, if data types 60 includes values of heart rate parameter and control data 60*a* that exceed an acuity limit 75 for heart rate data, then application 46 may assign an acuity classification 80*a* indicating a high patient acuity level. If the values of heart rate parameter and control data 60*a* are below the acuity limit 75 for heart rate data, then application 46 may assign an acuity classification 80*a* indicating a lower patient acuity level. Similarly, application 46 may assign a data classification 80*b* indicating a higher or lower acuity level depending on whether values of alarm data 60*b* exceed the acuity limits for alarm data 60*b*. Application 46 may also assign an acuity classification 80*c* indicating a higher or lower acuity level depending on whether values of waveform data 60*c* exceed an acuity limit 75 for any other data mentioned above such as device type and device location.

Application 46 determines a statistical weight value 90 for values of data types 60 having an assigned acuity classification 80. Statistical weight values 90 are used to provide a structure under which varying levels of data priority may be adaptively determined by a weighted sum calculation. According to an embodiment wherein node 20 is a patient monitoring device transmitting patient data over network 10 in a medical facility, it is envisioned that corresponding statistical weight values 90 are established for each of the various patient acuity-based acuity classifications 80 based on the priority to be accorded to each of these data classifications 80. By way of example, if data type 60 includes values of heart rate parameter and control data 60*a* to be transmitted that are assigned an acuity classification 80*a* indicating a high patient acuity level, then application 46 determines that a corresponding statistical weight value 90*a* is appropriate. In this particular circumstance, the determined value of statistical weight value 90*a* is higher than if the values of heart rate parameter and control data 60*a* to be transmitted are assigned an acuity classification 80*a* indicating a lower patient acuity level. Statistical weight values 90*b* are established for the various alarm acuity classifications 80*b*, and statistical weight values 90*c* are established for the various waveform acuity classifications 80*c*. According to an embodiment, statistical weight values 90*b* established for alarm acuity classifications 80*b* may be higher than statistical weight values 90*c* established for waveform acuity classifications 80*c*, which in turn may be higher than statistical weight values 90*a* established for parameter and control acuity classifications 80*a*. Similarly, statistical weight values may be established for other acuity classifications such as device type and location data.

Application 46 also performs a weighted-sum calculation 92 of all of the statistical weight values in order to determine whether a patient acuity threshold 94 is exceeded. Various types of weighted sum calculation techniques may be employed, such as linear, non-linear and geometric weighted sum calculations. The weighted sum calculation 92 factors in each of the various statistical weight values 90 assigned to the various values of data types 60 and calculates an overall sum. In this way, data type values 60 corresponding to high patient acuity levels will increase the overall weighted sum 92, and correspondingly increase the probability of the data being transmitted over network 10. Data type values 60 corresponding to lower acuity levels will decrease the overall weighted sum 92. As stated previously, it is contemplated that there may be more than two wireless network protocols available to the network 10, having varying reliabilities. In such cases, and still referring to FIG. 2, the patient acuity threshold 94 may be separated into specific ranges of acuity, such that the weighted sum acuity level 92 is compared against the ranges of the patient acuity threshold 94, and then assigned the appropriate reliability wireless protocol.

Figure 3:
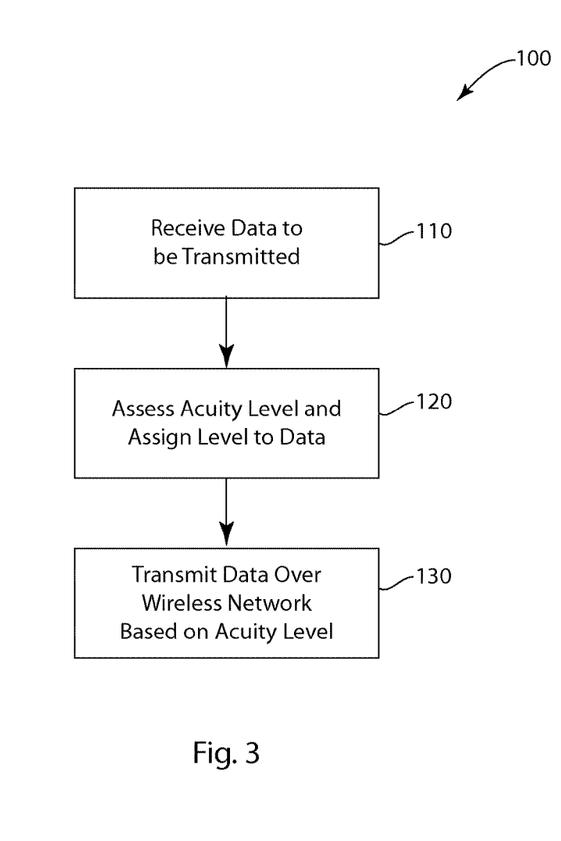
FIG. 3 is a flow chart illustrating an exemplary method in accordance with an embodiment.

Referring now to FIG. 3, a flow chart illustrating a method 100 in accordance with an embodiment is shown. Method 100 may be implemented in, for example, the network shown in FIG. 1 and using, for example, the process described above with respect to FIG. 2. At a step 110, data to be transmitted over a network is received. According to an embodiment, the data is acquired by a node 20 configured for wireless communication with an access point 14, 15. The node 20 may be configured for wireless communication with the access point 14, 15 according to IEEE 802.11e protocol, or configured for communication with a higher reliability network protocol, such as those mentioned previously. At a step 120, an acuity level is assessed and assigned to the data. The acuity level may be assigned by, for example, determining a classification for the data performing a weighted sum calculation based on the classification. At a step 130, the wireless protocol utilized is determined based on the acuity level.

In any given care unit or monitoring area, the condition of each patient is evaluated based on existing clinical indices/scores (such as MEWS, Apache, SOFA or the acuity level method described above. The patients are then ranked according to acuity.

In a further embodiment of the present application, network conditions are optimal, all patient data is treated equally and each patient's transmission has equal access to the network. If the network is congested, the data from patients with the highest acuity is given preferred access to network resources.

Preferred access can be obtained through a number of different strategies: by selecting the best available spectrum as discussed above, adjusting the differentiated services control parameter in a network, and reducing the amount of data sent for lower acuity patients to allow higher bandwidth for higher acuity patients.

Figure 4:
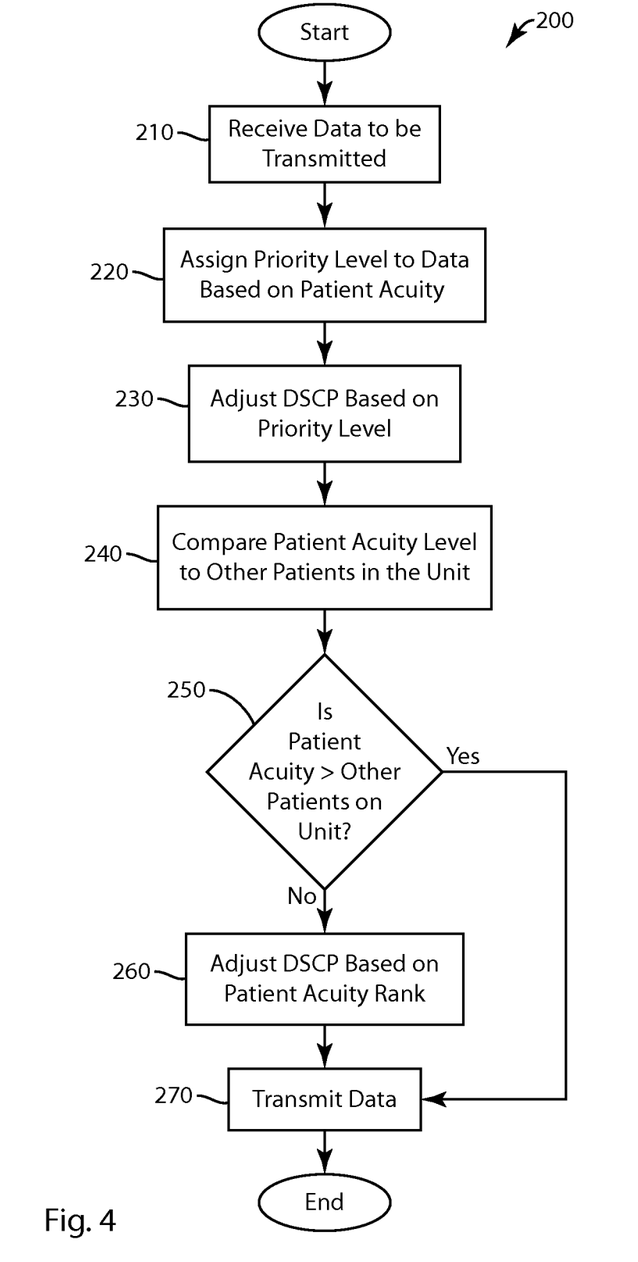
FIG. 4 is a flow chart illustrating an exemplary method in accordance with an with an embodiment.

Referring now to FIG. 4, a method 200 of an additional embodiment of the present application is illustrated in the flow chart. Once again, the method 200 may be implemented in, for example, the network shown in FIG. 1, and using, for example the process described above with respect to FIG. 2. In this method 200, data can be transmitted and is received in step 210, and a priority level is assigned to the data based on the patient acuity. The patient acuity of step 220 may be calculated through a number of known clinical indices/scores as described above, or may be determined by the weighted sum acuity 92 calculated in FIG. 2. In step 230, the differential services code point (DSCP) is adjusted based on this patient priority level, and the patient's acuity is compared to the level of other patients in the same unit or area. If the patient being monitored has an acuity level that is greater than the other patients monitored in that unit in step 250, then the data is transmitted over the wireless network. Still referring to FIG. 4, if the patient acuity is not greater than the other patients in the same unit or area of the monitoring group in step 250, then the DSCP is adjusted based on the patient acuity rank as compared to the other patients and the data is transmitted in step 270. Referring back to FIG. 2, this method 200 may be implemented between the step of the weighted sum of all data type acuity 92 and the patient acuity threshold exceeded 94. Of course, this is an example, and a portion of the method 200 may be implemented in whole or in part in the system such that patients are assigned priority levels based on their patient acuity score and their data transmitted according to their acuity rank.

Figure 5:
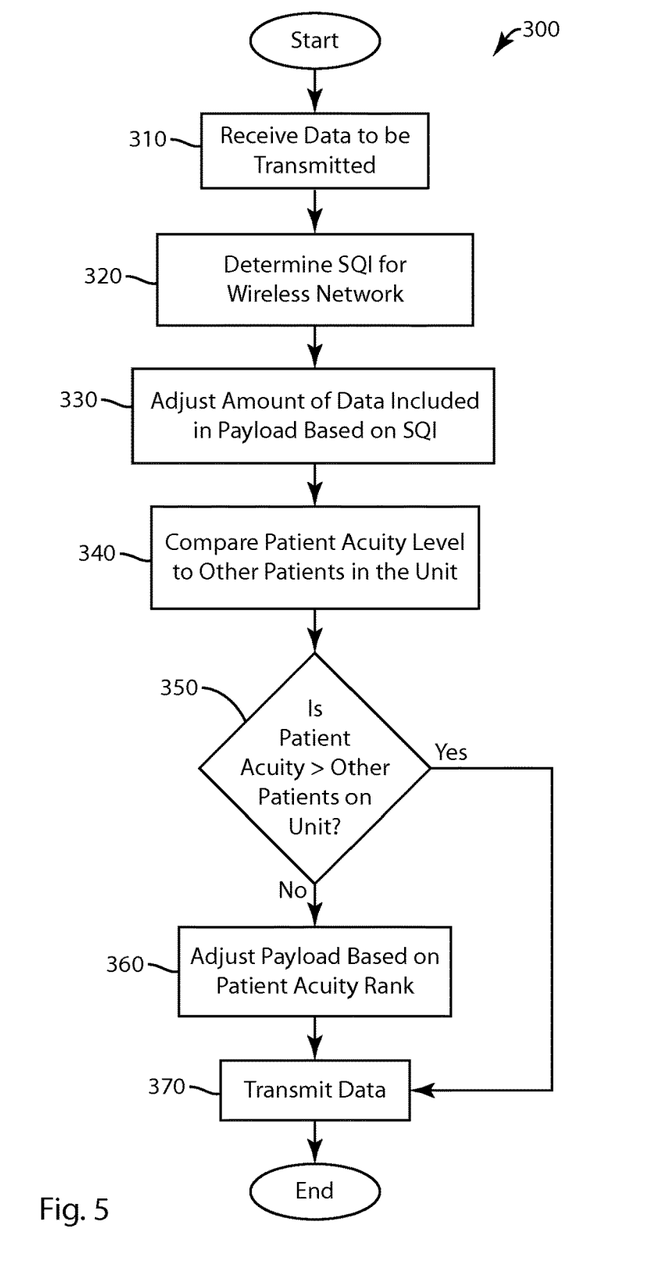
FIG. 5 is a flow chart illustrating an exemplary method in accordance with an embodiment.

Referring now to FIG. 5, a flow chart illustrating an additional method 300 in accordance with an additional embodiment is shown. Again, method 300 may be implemented in, for example, the network shown in FIG. 1 and using, for example, the process described above with respect to FIG. 2. Here, in step 300, data is received and a service quality index (SQI) is determined for the wireless network in step 320. In step 330, the amount of data included in payload, or data to be transferred is adjusted based on the SQI. In other words, if the wireless network has a high SQI then the data may be transmitted in its entirety. However, if the SQI is a low number, then a portion of the data may be removed from the data to be transmitted. In step 340, the patient's acuity level is compared to the level of other patients in the unit, and if the patient's acuity is greater than other patients in the monitoring unit, then the data is transmitted in step 370. If the patient's acuity is not greater than the other patients in the monitoring unit, then the payload of the data to be transmitted is adjusted based on the patient's acuity rank. In other words, the payload is reduced as the acuity level of the patient is reduced, and the data is transmitted accordingly in step 370. Once again, the method 300 of FIG. 5 may be implemented in whole or in part in portions of FIG. 2.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

In the foregoing description, certain terms have been used for brevity, clearness, and understanding. No unnecessary limitations are to be inferred therefrom beyond the requirement of the prior art because such terms are used for descriptive purposes and are intended to be broadly construed. The different configurations, systems, and method steps described herein may be used alone or in combination with other configurations, systems and method steps. It is to be expected that various equivalents, alternatives and modifications are possible within the scope of the appended claims.

What is claimed is:

1. A method of controlling transmission of patient data over a wireless network, comprising:
   determining an acuity level based on the patient data;
   comparing at a wireless network node the acuity level of the patient data to a plurality of acuity levels of other patient data in a monitoring area;
   selecting between at least a first wireless network protocol and a second wireless network protocol, wherein the first wireless network protocol has a higher reliability of the transmission of the patient data than the second wireless network protocol, and wherein the selection is made based on the comparison of the acuity level of the patient data to the plurality of acuity levels of the other patient data and the reliability; and
   transmitting the patient data over the wireless network using the selected wireless network protocol giving priority to the transmission of the patient data based on the comparison of the acuity level of the patient data to the plurality of acuity levels of the other patient data.

2. The method of claim 1, wherein the acuity level is determined at the wireless network node within the wireless network.

3. The method of claim 1, further comprising assigning a priority order for the transmission of an amount of the patient data based on the comparison, wherein the patient data with a higher acuity level is assigned a higher priority transmission using the first wireless network protocol.

4. The method of claim 1, wherein said determining the acuity level further includes:
   comparing the patient data to a set of acuity limits;
   assigning a classification to the patient data based on the comparison of the patient data to the set of acuity limits;
   applying a set of statistical weight values to the patient data based on the classification; and
   conducting a weighted sum calculation on the weighted patient data, wherein the weighted sum calculation outputs the acuity level.

5. The method of claim 1, wherein the first wireless network protocol has a lower bandwidth than the second wireless network protocol.

6. The method of claim 5, wherein the first wireless network protocol is a wireless medical telemetry service (WMTS) protocol and the second wireless network protocol is an IEEE 802.11 protocol.

7. The method of claim 1, further comprising determining whether the acuity level exceeds an acuity threshold, and selecting the first wireless network protocol when the acuity level exceeds the acuity threshold.

8. A node in a wireless network configured for wireless communication of patient data with an access point in the wireless network, the node comprising:
   a controller configured to:
      receive the patient data;
      determine an acuity level based on the patient data;
      compare the acuity level of the patient data to a plurality of acuity levels of other patient data in a monitoring area;
      select between at least a first wireless network protocol and a second wireless network protocol, wherein the first wireless network protocol has a higher reliability of a transmission of the patient data than the second wireless network protocol, and wherein the selection is made based on the comparison of the acuity level of the patient data to the plurality of acuity levels of the other patient data and the reliability;

assign a priority order for the transmission of an amount of the patient data based on the comparison, wherein the patient data with a higher acuity level is assigned a higher priority transmission using the first wireless network protocol; and transmit the patient data using the selected wireless network protocol.

9. The node of claim 8, wherein the first wireless network protocol has a lower bandwidth than the second wireless network protocol.

10. The node of claim 8, wherein the acuity level determination further includes:

comparing the patient data to a set of acuity limits;
assigning a classification to the patient data based on the comparison of the patient data to the set of acuity limits;
applying a set of statistical weight values to the patient data based on the classification; and
conducting a weighted sum calculation on the weighted values patient data, wherein the weighted sum calculation outputs the acuity level.

11. A network comprising:

an access point;
nodes configured for wireless communication of patient data with the access point;
wherein each of the nodes include a controller configured to:
receive the patient data;
determine an acuity level based on the patient data;
select between at least a first wireless network protocol and a second wireless network protocol, wherein the first wireless network protocol has a higher reliability of a transmission of the patient data than the second wireless network protocol, and wherein the selection is made based on a comparison of the acuity level of the patient data to a plurality of acuity levels of other patient data and the reliability;
transmit the patient data over the network using the selected wireless network protocol;
wherein the controller is configured to determine the acuity level by:
comparing the patient data to a set of acuity limits;
assigning a classification to the patient data based on the comparison of the patient data to the set of acuity limits;
applying a set of statistical weight values to the patient data based on the classification; and
conducting a weighted sum calculation on the weighted values patient data, wherein the weighted sum calculation outputs the acuity level.

12. The network of claim 11, wherein the first wireless network protocol has a lower bandwidth than the second wireless network protocol.

13. The network of claim 11, wherein the controller is further configured to compare the acuity level of the patient data to the plurality of acuity levels for the other patient data in a monitoring area and gives priority to the transmission of the patient data based on the comparison of the acuity level of the patient data to the plurality of acuity levels for the other patient data.

14. The network of claim 13, wherein controller is further configured to assign a priority order for the transmission of an amount of the patient data to the first or second wireless network protocol based on the acuity level of the patient data, wherein a higher acuity level is assigned a higher priority transmission using the first wireless network protocol.

15. The network of claim 11, wherein the first wireless network protocol is a wireless medical telemetry service (WMTS) protocol and the second wireless network protocol is an IEEE 802.11 protocol.

16. The network of claim 11, wherein the controller further selects the first wireless network protocol when the acuity level exceeds an acuity threshold.

* * * * *